(12) United States Patent
Freedman et al.

(10) Patent No.: US 8,262,710 B2
(45) Date of Patent: Sep. 11, 2012

(54) DYNAMIC STABILIZATION DEVICE FOR ANTERIOR LOWER LUMBAR VERTEBRAL FUSION

(75) Inventors: Scott Freedman, Sharon, MA (US); Charles Wing, Center Valley, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 960 days.

(21) Appl. No.: 11/585,760

(22) Filed: Oct. 24, 2006

(65) Prior Publication Data
US 2008/0177263 A1 Jul. 24, 2008

(51) Int. Cl.
*A61B 17/66* (2006.01)
*A61B 17/70* (2006.01)

(52) U.S. Cl. ...... 606/282; 606/280; 606/257; 623/17.11

(58) Field of Classification Search .............. 606/70–71, 606/280–299; 623/17.11–17.16
See application file for complete search history.

(56) References Cited

U.S. PATENT DOCUMENTS

| | | | |
|---|---|---|---|
| 500,165 A * | 6/1893 | Spooner | 66/195 |
| 4,127,904 A | 12/1978 | Junker | |
| 5,108,395 A | 4/1992 | Laurain | |
| 5,161,142 A | 11/1992 | Okano | |
| 5,364,399 A | 11/1994 | Lowery et al. | |
| 5,520,690 A | 5/1996 | Errico et al. | |
| 5,531,747 A | 7/1996 | Ray | |
| 5,549,607 A | 8/1996 | Olson et al. | |
| 5,549,612 A | 8/1996 | Yapp et al. | |
| 5,607,426 A | 3/1997 | Ralph et al. | |
| 5,616,142 A | 4/1997 | Yuan et al. | |
| 5,616,144 A | 4/1997 | Yapp et al. | |
| 5,676,666 A | 10/1997 | Oxland et al. | |
| 5,681,312 A | 10/1997 | Yuan et al. | |
| 5,702,395 A | 12/1997 | Hopf | |
| 5,800,433 A | 9/1998 | Yuan et al. | |
| 5,843,082 A * | 12/1998 | Yuan et al. | 606/250 |
| 5,876,402 A | 3/1999 | Errico et al. | |
| 5,904,683 A | 5/1999 | Pohndorf et al. | |
| 5,954,722 A | 9/1999 | Bono | |
| 6,030,389 A | 2/2000 | Wagner et al. | |
| 6,036,693 A * | 3/2000 | Yuan et al. | 606/250 |
| 6,045,552 A * | 4/2000 | Zucherman et al. | 606/86 B |
| 6,066,036 A | 5/2000 | Carollo | |

(Continued)

FOREIGN PATENT DOCUMENTS
DE 40 38 082 C2 9/1992
(Continued)

OTHER PUBLICATIONS

European Search Report dated Jan. 30, 2008.
(Continued)

*Primary Examiner* — Thomas Barrett
*Assistant Examiner* — Matthew Lawson
(74) *Attorney, Agent, or Firm* — RatnerPrestia

(57) ABSTRACT

A dynamic vertebral stabilization device for constraining motion of adjacent vertebrae is provided. The bone stabilization device comprises a first plate having a vertebral mating surface for positioning against a vertebrae, wherein the first plate defines a recess. The device further comprises a second plate having a vertebral mating surface for positioning against an adjacent vertebrae. The second plate includes a projection configured to travel in the recess of the first plate. The vertebral mating surface of the first plate is non-coplanar with respect to the vertebral mating surface of the second plate.

16 Claims, 10 Drawing Sheets

U.S. PATENT DOCUMENTS

| | | | | |
|---|---|---|---|---|
| 6,106,527 | A * | 8/2000 | Wu et al. | 606/250 |
| 6,117,135 | A | 9/2000 | Schlapfer | |
| 6,139,550 | A | 10/2000 | Michelson | |
| 6,152,927 | A | 11/2000 | Farris et al. | |
| 6,193,720 | B1 | 2/2001 | Yuan et al. | |
| 6,193,721 | B1 | 2/2001 | Michelson | |
| 6,206,881 | B1 | 3/2001 | Frigg et al. | |
| 6,224,602 | B1 | 5/2001 | Hayes | |
| 6,228,085 | B1 * | 5/2001 | Theken et al. | 606/289 |
| 6,235,033 | B1 | 5/2001 | Brace et al. | |
| 6,235,034 | B1 | 5/2001 | Bray | |
| 6,258,089 | B1 | 7/2001 | Campbell et al. | |
| 6,280,445 | B1 | 8/2001 | Morrison et al. | |
| 6,293,949 | B1 | 9/2001 | Justis et al. | |
| 6,306,136 | B1 | 10/2001 | Baccelli | |
| 6,331,179 | B1 | 12/2001 | Freid et al. | |
| 6,340,362 | B1 | 1/2002 | Pierer et al. | |
| 6,398,783 | B1 | 6/2002 | Michelson | |
| 6,402,756 | B1 * | 6/2002 | Ralph et al. | 606/71 |
| 6,413,259 | B1 | 7/2002 | Lyons et al. | |
| 6,454,769 | B2 | 9/2002 | Wagner et al. | |
| 6,503,250 | B2 | 1/2003 | Paul | |
| 6,527,776 | B1 | 3/2003 | Michelson | |
| 6,533,786 | B1 | 3/2003 | Needham et al. | |
| 6,565,571 | B1 * | 5/2003 | Jackowski et al. | 606/86 B |
| 6,585,769 | B1 | 7/2003 | Muhanna et al. | |
| 6,595,993 | B2 | 7/2003 | Donno et al. | |
| 6,599,290 | B2 | 7/2003 | Bailey et al. | |
| 6,602,255 | B1 | 8/2003 | Campbell et al. | |
| 6,602,256 | B1 | 8/2003 | Hayes | |
| 6,613,053 | B1 | 9/2003 | Collins et al. | |
| 6,626,907 | B2 | 9/2003 | Campbell et al. | |
| 6,645,207 | B2 | 11/2003 | Dixon et al. | |
| 6,652,525 | B1 | 11/2003 | Assaker et al. | |
| 6,666,867 | B2 * | 12/2003 | Ralph et al. | 606/71 |
| 6,679,883 | B2 | 1/2004 | Hawkes et al. | |
| 6,682,530 | B2 | 1/2004 | Dixon et al. | |
| 6,689,134 | B2 * | 2/2004 | Ralph et al. | 606/71 |
| 6,755,833 | B1 | 6/2004 | Paul et al. | |
| 6,761,719 | B2 | 7/2004 | Justis et al. | |
| 6,780,186 | B2 | 8/2004 | Errico et al. | |
| 6,852,113 | B2 | 2/2005 | Nathanson et al. | |
| 6,890,335 | B2 | 5/2005 | Grabowski et al. | |
| 6,932,820 | B2 | 8/2005 | Osman | |
| 6,945,973 | B2 | 9/2005 | Bray | |
| 6,964,664 | B2 | 11/2005 | Freid et al. | |
| 6,989,013 | B2 | 1/2006 | Pisharodi | |
| 7,008,427 | B2 | 3/2006 | Sevrain | |
| 7,025,769 | B1 | 4/2006 | Ferree | |
| 7,041,105 | B2 | 5/2006 | Michelson et al. | |
| 7,048,739 | B2 | 5/2006 | Konieczynski et al. | |
| 7,097,645 | B2 | 8/2006 | Michelson et al. | |
| 7,115,142 | B2 | 10/2006 | Muhanna et al. | |
| 7,118,573 | B2 | 10/2006 | Michelson | |
| 7,137,984 | B2 | 11/2006 | Michelson | |
| 7,169,150 | B2 | 1/2007 | Shipp et al. | |
| 7,175,623 | B2 | 2/2007 | Thramann et al. | |
| 7,214,226 | B2 | 5/2007 | Alleyne | |
| 7,291,152 | B2 * | 11/2007 | Abdou | 606/279 |
| 7,341,590 | B2 * | 3/2008 | Ferree | 606/915 |
| 7,666,185 | B2 * | 2/2010 | Ryan et al. | 606/71 |
| 2002/0049394 | A1 * | 4/2002 | Roy et al. | 600/594 |
| 2003/0044001 | A1 | 3/2003 | Kim | |
| 2003/0074001 | A1 * | 4/2003 | Apfelbaum et al. | 606/71 |
| 2003/0105462 | A1 | 6/2003 | Haider | |
| 2003/0114856 | A1 | 6/2003 | Nathanson et al. | |
| 2003/0187443 | A1 | 10/2003 | Lauryssen et al. | |
| 2003/0208204 | A1 | 11/2003 | Bailey et al. | |
| 2003/0212399 | A1 | 11/2003 | Dinh et al. | |
| 2003/0229348 | A1 | 12/2003 | Sevrain | |
| 2004/0006343 | A1 | 1/2004 | Sevrain | |
| 2004/0019353 | A1 | 1/2004 | Freid et al. | |
| 2004/0039387 | A1 | 2/2004 | Gause et al. | |
| 2004/0092939 | A1 | 5/2004 | Freid et al. | |
| 2004/0106924 | A1 | 6/2004 | Ralph et al. | |
| 2004/0127896 | A1 | 7/2004 | Lombardo et al. | |
| 2004/0127904 | A1 | 7/2004 | Konieczynski et al. | |
| 2004/0158251 | A1 | 8/2004 | Morrison et al. | |
| 2004/0167521 | A1 | 8/2004 | DeWindt | |
| 2004/0204712 | A1 | 10/2004 | Kolb et al. | |
| 2004/0204713 | A1 | 10/2004 | Abdou | |
| 2004/0210221 | A1 * | 10/2004 | Kozak et al. | 606/69 |
| 2004/0210223 | A1 | 10/2004 | Pisharodi | |
| 2004/0215192 | A1 | 10/2004 | Justis et al. | |
| 2004/0220571 | A1 | 11/2004 | Assaker et al. | |
| 2005/0004573 | A1 * | 1/2005 | Abdou | 606/61 |
| 2005/0043732 | A1 | 2/2005 | Dalton | |
| 2005/0049593 | A1 | 3/2005 | Dnoung et al. | |
| 2005/0049595 | A1 | 3/2005 | Suh | |
| 2005/0075633 | A1 | 4/2005 | Ross | |
| 2005/0107795 | A1 | 5/2005 | Morris et al. | |
| 2005/0124966 | A1 | 6/2005 | Karpowicz et al. | |
| 2005/0137597 | A1 | 6/2005 | Butler et al. | |
| 2005/0149026 | A1 * | 7/2005 | Butler et al. | 606/69 |
| 2005/0177160 | A1 | 8/2005 | Baynham et al. | |
| 2005/0182404 | A1 | 8/2005 | Lauryssen et al. | |
| 2005/0187553 | A1 | 8/2005 | Grabowski et al. | |
| 2005/0216010 | A1 | 9/2005 | Michelson | |
| 2005/0216011 | A1 | 9/2005 | Paul | |
| 2005/0240184 | A1 | 10/2005 | Osman | |
| 2005/0261682 | A1 * | 11/2005 | Ferree | 606/61 |
| 2005/0267579 | A1 * | 12/2005 | Reiley et al. | 623/17.11 |
| 2005/0283155 | A1 | 12/2005 | Jacene et al. | |
| 2006/0009845 | A1 * | 1/2006 | Chin | 623/17.11 |
| 2006/0064097 | A1 | 3/2006 | Bray | |
| 2006/0079901 | A1 | 4/2006 | Ryan et al. | |
| 2006/0100625 | A1 | 5/2006 | Ralph et al. | |
| 2006/0100626 | A1 | 5/2006 | Rathbun et al. | |
| 2006/0106387 | A1 | 5/2006 | Fanger et al. | |
| 2006/0116681 | A1 | 6/2006 | Bert | |
| 2006/0116683 | A1 | 6/2006 | Barrall et al. | |
| 2006/0122602 | A1 | 6/2006 | Konieczynski et al. | |
| 2006/0122604 | A1 | 6/2006 | Gorhan et al. | |
| 2006/0122606 | A1 | 6/2006 | Wolgen | |
| 2006/0122607 | A1 | 6/2006 | Kolb | |
| 2006/0142767 | A1 | 6/2006 | Green et al. | |
| 2006/0142768 | A1 | 6/2006 | Paul et al. | |
| 2006/0149254 | A1 * | 7/2006 | Lauryssen et al. | 606/69 |
| 2006/0161157 | A1 | 7/2006 | Mosca et al. | |
| 2006/0167456 | A1 | 7/2006 | Johnson et al. | |
| 2006/0195100 | A1 | 8/2006 | Kirschman | |
| 2006/0200147 | A1 | 9/2006 | Ensign et al. | |
| 2006/0217724 | A1 | 9/2006 | Suh | |
| 2006/0217725 | A1 | 9/2006 | Suh | |
| 2006/0235398 | A1 * | 10/2006 | Farris et al. | 606/69 |
| 2006/0235405 | A1 * | 10/2006 | Hawkes | 606/69 |
| 2006/0235409 | A1 | 10/2006 | Blain | |
| 2006/0241616 | A1 | 10/2006 | Konieczynski et al. | |
| 2006/0271052 | A1 | 11/2006 | Stern | |
| 2007/0016206 | A1 | 1/2007 | Thramann et al. | |
| 2007/0293864 | A1 | 12/2007 | Reimels et al. | |
| 2008/0147125 | A1 | 6/2008 | Colleran et al. | |
| 2008/0154312 | A1 | 6/2008 | Colleran et al. | |
| 2008/0208260 | A1 | 8/2008 | Truckai et al. | |
| 2008/0234676 | A1 | 9/2008 | Schulze et al. | |
| 2008/0234681 | A1 | 9/2008 | Baynham | |
| 2008/0306550 | A1 | 12/2008 | Matityahu | |
| 2009/0012569 | A1 | 1/2009 | Dall et al. | |

FOREIGN PATENT DOCUMENTS

| | | |
|---|---|---|
| DE | 42 01 043 C2 | 7/1993 |
| DE | 696 29 605 T2 | 8/1996 |
| DE | 693 20 593 T2 | 4/1997 |
| DE | 100 03 968 A1 | 8/2001 |
| DE | 101 32 712 B4 | 1/2003 |
| DE | 10 2005 044 532 A1 | 4/2007 |
| EP | 0 506 420 B1 | 9/1992 |
| EP | 0 637 437 A1 | 2/1995 |
| EP | 1 348 390 A2 | 10/2003 |
| EP | 1 488 753 B1 | 12/2004 |
| FR | 2 651 992 | 3/1991 |
| FR | 2 784 571 | 4/2000 |
| WO | WO 93/01772 A1 | 2/1993 |
| WO | WO 2005/086708 | 9/2005 |
| WO | WO/2006107891 | 10/2006 |

OTHER PUBLICATIONS

USPTO Office Action dated Mar. 24, 2009 for U.S. Appl. No. 11/836,439.

USPTO Office Action dated May 27, 2009 for U.S. Appl. No. 11/836,439.

USPTO Office Action dated Oct. 5, 2009 for U.S. Appl. No. 11/836,439.

*Biomechanical Study on the Effect of Cervical Spine Fusion on Adjacent-Level Intradiscal Pressure and Segmental Motion*; Jason C. Eck, Do, S. Craig Humphreys, MD, Tae-Hong Lim, PhD, Soon Tack Jeong, MD, Jesse G. Kim, MS, Scott D. Hodges, Do, Howard S. An, MD; *Spine* vol. 27, No. 22, pp. 2431-2434; © 2002, Lippincott Williams & Wilkins, Inc.

Segmental Motion Adjacent to Anterior Cervical Arthrodesis (A Prospective Study); Frode Kolstad, MD, Øystein P. Nygaard, MS, PhD; Gunnar Leivseth, Md, PhD; *Spine* vol. 32, No. 5, pp. 512-517, © 2007, Lippincott Williams & Wilkins, Inc.

*Biomechanical Comparison of Adjacent Segmental Motion After Ventral Cervical Fixation With Varying Angles of Lordosis*; Soo-Hyun Hwang, MD, Mark Kayanja, MD,PHD, Ryan A. Milks, BSBME, Edward C. Benzel, MD,*The Spine Journal* 7 (2007) 216-221.

*Adjacent Segment Degeneration and Adjacent Segment Disease: The Consequences of Spinal Fusion?*; Alan S. Hilibrand, MD, Matthew Robbins, BA; *The Spine Journal* 4 (2004) 190S-194S.

*The Effect of Compressive Force Applied to the Intervertebral Disc in Vivo: A Study of Proteoglycans and Collagen*; Hutton, William C. DSc; Toribatake, Yasumitsu MD, Elmer, William A. PhD; Ganey, Timothy M. PhD, Tomita, Katsuro Md, Whitesides Thomas E. MD; *Spine* vol. 23(23), Dec. 1, 1998, pp. 2524-2537.

\* cited by examiner

DYNAMIC STABILIZATION DEVICE FOR ANTERIOR LOWER LUMBAR VERTEBRAL FUSION

FIELD OF THE INVENTION

The present invention relates to a dynamic stabilization device for anterior lower lumbar vertebral fusion, and a method for installing the dynamic stabilization device to the lower lumbar vertebrae.

BACKGROUND OF THE INVENTION

The human spine is composed of cervical, thoracic, lumbar and sacrum vertebrae. The neck region of the spine is known as the cervical spine, which consists of seven vertebrae, which are abbreviated C1 through C7 (top to bottom). Beneath the last cervical vertebra are twelve vertebrae of the thoracic spine. The thoracic vertebrae are abbreviated T1 through T12 (top to bottom). Beneath the last thoracic vertebra are five lumbar vertebrae, abbreviated L1 through L5. The size and shape of each lumbar vertebra is designed to carry most of the body's weight. Each structural element of a lumbar vertebra is bigger, wider and broader than similar components in the cervical and thoracic regions. Beneath the lumbar spine, five sacral vertebrae, abbreviated S1 through S5, grow together to form the triangular bone called the sacrum. The lowest four vertebrae beneath the sacrum form the tailbone or coccyx.

A typical vertebra consists of two essential parts, i.e., an anterior (front) segment, which is the vertebral body, and a projectionerior part which encloses the vertebral foramen. When the vertebrae are articulated with each other, the bodies form a strong pillar for the support of the head and trunk.

The cervical, thoracic and lumbar vertebrae and sacrum are separated by intervertebral discs. For example, the intervertebral disc located at the interface between the largest lumbar vertebrae (L5) and the first sacral vertebrae (S1) is commonly referred to as the L5/S1 disc. An intervertebral disc is composed of a tough, fibrous ring, commonly referred to as the annulus fibrosus, which is wrapped around a jelly-like center, commonly referred to as the nucleus pulposus.

The intervertebral discs are exposed to a variety of forces and stress depending upon the position and movement of the body, and position of the disc within the body. Because the spine supports the weight of the body, axial compressive forces are constantly applied to the discs, in either a standing or sitting pose of the body. Furthermore, the intervertebral discs are exposed to additional forces and stress resulting from contortion of the body, for example, flexion (i.e., bending forward), extension (i.e., bending backward), lateral bending (i.e., bending to either side), and torsional movement (i.e., upper body twist) of the body. Furthermore, discs that rest on an angled plane are exposed to shear stress. Generally, the steeper the angle of the disc, the greater the shear stress imparted on that disc. For example, the L5/S1 disc resides on the steepest plane of all the discs of the spine. It follows that the L5/S1 disc is exposed to the greatest compressive force and shear stress of all the spinal discs because the L5/S1 disc is the lowest disc in the spine. For the foregoing reasons the L5/S1 disc is particularly prone to bulging, herniation, deformity, or deterioration under the aforementioned compressive force, shear stress, or trauma.

Pain caused by a herniated, bulging, deformed, or disintegrated lumbar disc at either the L4/L5 or L5/S1 is commonly known as sciatica. The sciatic nerve exits the spinal column between the lowest lumbar vertebral body (L5) and first vertebrae of the sacrum (S1). Compression, inflammation or irritation of the sciatic nerve due to contact with a herniated disc or misaligned vertebrae is a common cause of pain. Discectomy surgery to remove the L5/S1 disc and replace it with a fusion ALIF spacer is often employed to relieve the pain of sciatica.

The degenerated L5/S1 disc (or any other lumbar disc) may be replaced with an anterior lumbar interbody fusion ALIF spacer, hereinafter ALIF spacer. The ALIF procedure is similar to a posterior lumbar interbody fusion (PLIF), except that in an ALIF procedure the disc space is fused by approaching the spine through the abdomen instead of through the lower back.

Common ALIF spacers include a hollow center that is pre-filled with bone graft, such as an autograft, allograft, synthetic bone substitute, or bone morphogenic protein (BMP). Such a graft is intended to accelerate the biological fusion of adjacent vertebrae. Specifically, nutrient blood vessels which form between the vertebrae and within the ALIF spacer stimulate bone growth. In the presence of the nutrient blood vessels, the vertebrae fuse with the graft and ultimately fuse together. Furthermore, it has been found that the nutrient blood vessels form more rapidly when the adjacent vertebrae are appropriately loaded.

In an unspecified percentage of ALIF procedures, the vertebrae fail to fuse together due to either lack of nutrient blood vessel generation or lack of axial compressive load between the vertebrae (stress shielding). It is generally held that excessive extension, flexion, torsion, lateral movement, and shear stresses applied to the ALIF spacer interrupt formation of the nutrient blood vessels, thereby inhibiting fusion of the vertebrae.

In the interest of improving discectomy procedures, particularly ALIF procedures, vertebral stabilization devices have been devised to maintain the graft in a state of compression as well as restrict flexion, extension, lateral, torsional, and shear motion of the adjacent vertebrae (a diagram of the motions are illustrated in FIG. 1B).

In general, three types of stabilization devices currently exist. First, stabilization devices that support all of the vertebra rendering no force on the intervertebral graft are called "stress shielding" devices. Second, stabilization devices that support or share a portion of the spinal load in parallel with the graft are called load sharing devices. Finally, stabilization devices that allow axial subsidence of the implant and support most of the load on the individual bone grafts are referred to as dynamized stabilization devices. This invention focuses on dynamized stabilization devices. For example, a dynamized stabilization device is disclosed in U.S. Pat. No. 6,645,207 to Dixon et al., which is incorporated herein by reference in its entirety. However, a need exists for a dynamized stabilization device that conforms to the unique anatomical constraints of the lower lumbar region of the spine.

SUMMARY OF THE INVENTION

According to one aspect of the invention a dynamic vertebral stabilization device for constraining motion of adjacent vertebrae is provided. The bone stabilization device comprises a first plate having a vertebral mating surface for positioning against a vertebrae, wherein the first plate defines a recess. The device further comprises a second plate having a vertebral mating surface for positioning against an adjacent vertebrae. The second plate includes a projection configured to travel in the recess of the first plate. The vertebral mating surface of the first plate is non-coplanar with respect to the vertebral mating surface of the second plate.

According to another aspect of the invention, the first plate defines a thru-hole, and the second plate includes a projection configured to travel in the thru-hole of the first plate.

According to still another aspect of the invention a method of installing a dynamic vertebral stabilization device comprising a superior plate and an inferior plate onto adjacent vertebrae is provided. The method comprises the step of coupling the superior plate to the inferior plate. The method further comprises the steps of mounting the superior plate to a lumbar vertebrae, and mounting the inferior plate to a sacral vertebrae.

BRIEF DESCRIPTION OF THE DRAWINGS

The invention is best understood from the following detailed description when read in connection with the accompanying drawing. It is emphasized that, according to common practice, the various features of the drawing may not be to scale. Included in the drawing are the following figures.

DETAILED DESCRIPTION OF THE INVENTION

Figure 1A:
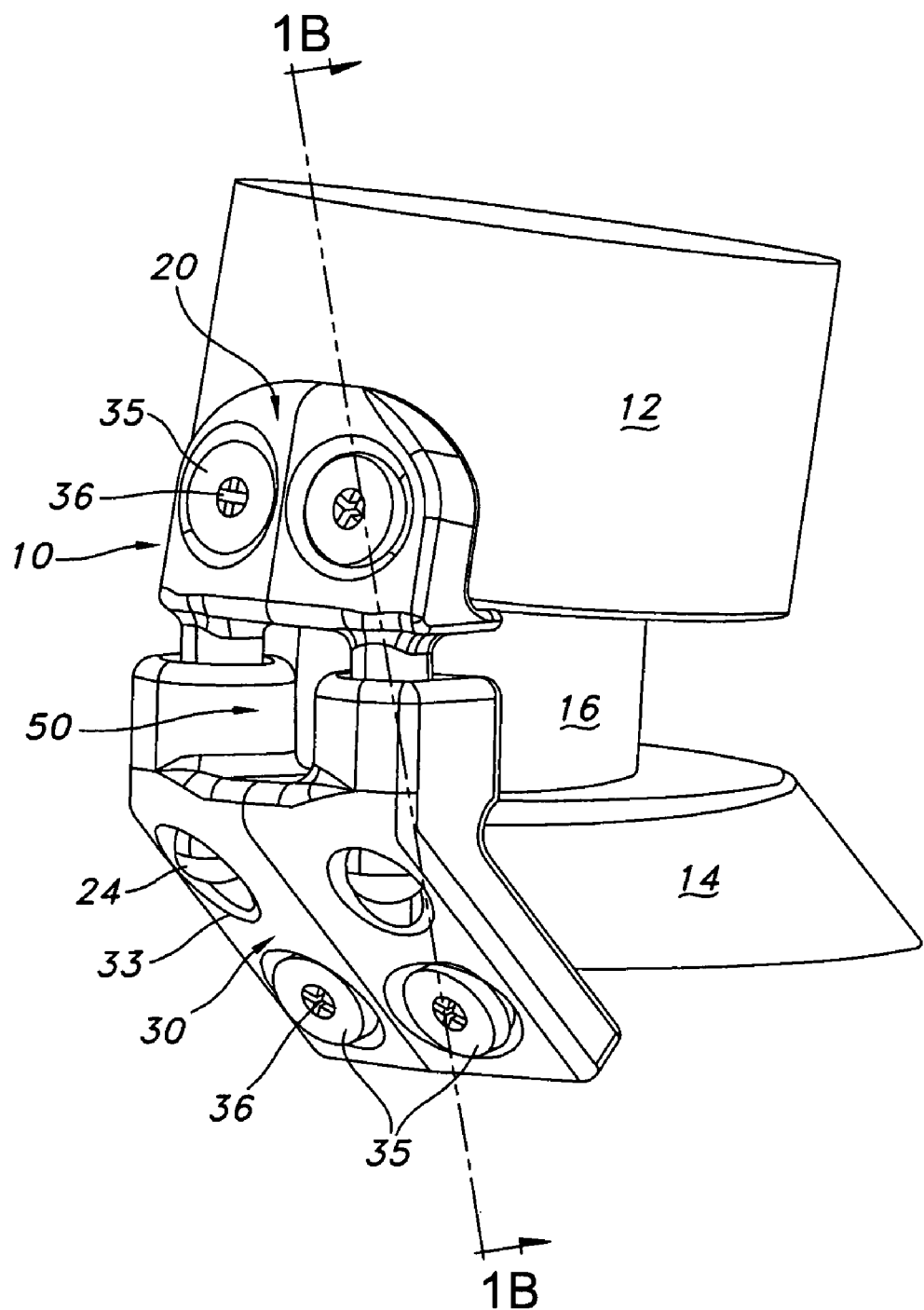
FIG. 1A is a perspective view of a dynamic vertebral stabilization device mounted to the L5 and S1 vertebrae, according to one exemplary embodiment of the invention.

The invention will next be illustrated with reference to the Figures. Such Figures are intended to be illustrative rather than limiting and are included herewith to facilitate explanation of the present invention. The Figures are not necessarily to scale, and are not intended to serve as engineering drawings.

Referring generally to the figures, according to an aspect of the invention, a bone stabilization device 10, 110, 210 comprises an inferior plate 30, 130, 230 having a vertebral mating surface 31 for positioning against a vertebrae 14, and the inferior plate defines a recess 33, 133. The device further comprises a superior plate 20, 120, 220 having a vertebral mating surface 21 for positioning against an adjacent vertebrae 12. The superior plate includes a projection 24 configured to travel in the recess 33, 133 of the inferior plate. The vertebral mating surface 31 of the inferior plate is non-coplanar with respect to the vertebral mating surface 21 of the superior plate.

According to still another aspect of the invention, a method of installing a dynamic vertebral stabilization device 10 comprising a superior plate 20 and an inferior plate 30 onto adjacent vertebrae 12 and 14 is provided. The method comprises the step of coupling the superior plate 20 to the inferior plate 30. The method further comprises the steps of mounting the superior plate 20 to a lumbar vertebrae 12, and mounting the inferior plate 30 to a sacral vertebrae 14.

Referring now to FIG. 1A, an exemplary embodiment of a dynamic vertebral stabilization device 10 is shown fixedly mounted to the anterior side of the L5 and S1 vertebrae. The dynamic vertebral stabilization device 10 is also referred to herein as vertebral stabilization device 10, stabilization device 10, and device 10. The L5 vertebrae is denoted by numeral 12, and the S1 vertebrae is denoted by numeral 14. An ALIF spacer interposed between vertebrae 12 and 14 is denoted by numeral 16.

The exemplary device 10 is referred to as 'dynamic' or 'dynamized' because it permits compression and expansion of vertebrae 12 and 14. Additionally, device 10 is referred to as a 'stabilization device' because it limits flexion, extension, torsion, lateral motion, and shear motion of adjacent vertebrae 12 and 14, relative to each other, as explained in greater detail with reference to FIG. 1B.

The stabilization device 10 comprises a superior plate 20 and an inferior plate 30. The terms 'superior' and 'inferior' refer to the relative positions of the plates, i.e., in general, a superior component is positioned on the spine at an elevation above an inferior component. In this embodiment, the superior plate 20 is fixedly mounted to vertebrae 12 by two fasteners 35, and similarly, inferior plate 30 is fixedly mounted to vertebrae 14 by two fasteners 35. The superior plate 20 is slideably engaged with inferior plate 30, such that the plates may translate relative to each other, as explained in greater detail with reference to the other figures.

A graft window 50 is exposed between the plates 20 and 30. In practice, the window 50 is intended for viewing and accessing ALIF spacer 16. The graft window 50 permits access to and/or visualization of the bone graft area, i.e., the area of spacer 16, after attachment of ALIF spacer 16. The height of the graft window increases and decreases with respective expansion and contraction of the dynamic device. The graft window 50 is a particularly beneficial feature of device 10 because it provides access to ALIF spacer 16 even after device 10 is installed onto the spine. In this regard, the surgeon may view the position and/or readjust the position of ALIF spacer 16 through window 50, without removing device 10 from the spine. The length and width of the window is preferably, but not necessarily, sized for maximum exposure of the graft area without compromising the strength of device 10.

Figure 1B:
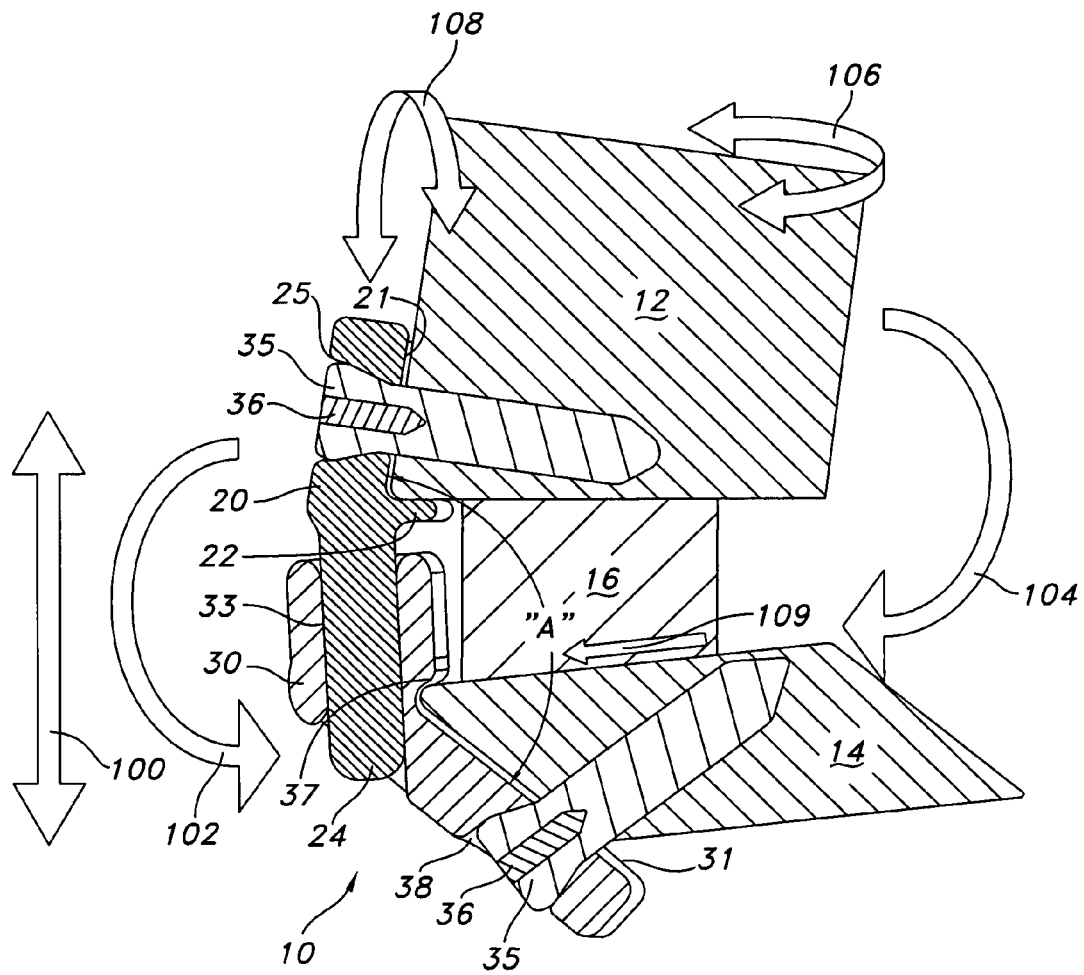
FIG. 1B is a cross-sectional view of the dynamic vertebral stabilization device of FIG. 1A taken along the lines 1B-1B.

Referring now to FIG. 1B, a cross sectional view of FIG. 1A taken along the lines 1B-1B is shown. The stabilization device 10 is uniquely adapted for constraining relative motion of a lumbar vertebrae (e.g., L5 vertebrae 12) and a sacral vertebrae (e.g., S1 vertebrae 14). The vertebral mating surface 21 of superior plate 20 is mounted to the anterior surface of L5 vertebrae 12, and vertebral mating surface 31 of inferior plate 30 is mounted to the anterior surface of S1 vertebrae 14.

The transition between the lumbar and sacral vertebrae is unique. Unlike other vertebrae of the spine, the L5 and S1 vertebrae are axially misaligned to a relatively substantial degree, i.e., the longitudinal axes of vertebrae 12 and 14 are misaligned with respect to each other. In order to conform to the axial misalignment of vertebrae 12 and 14, the vertebral mating surfaces 21 and 31 of device 10 are generally non-coplanar with respect to each other. The vertebral mating surfaces 21 and 31 of the plates are separated by an angle "A", as shown in FIG. 1B. According to one exemplary embodiment, angle "A" ranges from about 110° to about 170° degrees. According to another exemplary embodiment, angle "A" ranges from about 130° to about 150° degrees. However, it should be understood that angle "A" may comprise any dimension to conform to varying patient anatomy.

The range of motion of the human spine is denoted by arrows 100 through 109. The human spine is capable of six degrees of freedom, including compression and expansion along axis 100, flexion (i.e., bending forward) denoted by arrow 102, extension (i.e., bending backward) denoted by arrow 104, torsion (i.e., upper body twist) denoted by arrows 106, lateral motion (i.e., bending from side to side) denoted by arrows 108, and shear motion and stress such as that depicted along arrow 109. As mentioned above, shear motion results from the interface angle of adjacent vertebrae, and the position of the disc with respect to the center of gravity of the body. The lumbar discs are generally exposed to the greatest shear stress of all the vertebral discs, and with regard to the interspace, shear force 109 is generally concentrated in a direction parallel to the superior surface of S1 vertebrae 14, as shown in FIG. 1B.

In view of the foregoing, stabilization device 10 was developed to facilitate compression of adjacent vertebrae 12 and 14 along axis 100, while limiting flexion (arrow 102), extension (arrow 104), torsion (arrows 106), lateral motion (arrows 108), and shear motion and stress (arrow 109) of adjacent vertebrae, to encourage fusion of the vertebrae through spacer 16.

The stabilization device 10 permits dynamic compression and expansion of vertebrae 12 and 14 along axis 100. To facilitate relative motion of adjacent vertebrae 12 and 14 along axis 100, device 10 includes projections 24 that are slideably carried in complimentary recesses 33. Specifically, projections 24 of superior plate 20 telescope within recesses 33 of inferior plate 30 along axis 100. It follows that the longitudinal axis of both projections 24 and recesses 33 are oriented substantially parallel to axis 100.

The ALIF spacer 16 is compressed between vertebrae 12 and 14 as the vertebrae converge along axis 100. Maintaining ALIF spacer 16 in a state of compression encourages the formation of nutrient blood vessels, and ultimately promotes fusion of the stabilized vertebrae 12 and 14. To maximize compression of ALIF spacer 16 along axis 100, the top and bottom planar surfaces of ALIF spacer 16 are substantially orthogonal to axis 100, such that the compressive forces applied by the adjacent vertebrae are directly transferred to ALIF spacer 16.

In addition to being dynamic, the device 'stabilizes' the adjacent vertebrae by limiting flexion (arrow 102), extension (arrow 104), torsion (arrow 106), lateral motion (arrow 108), and shear motion (arrow 109) of adjacent vertebrae 12 and 14, relative to each other. Extension, flexion, torsion, lateral motion, and/or shearing motion applied to ALIF spacer 16 interrupt formation of the nutrient blood vessels, thereby inhibiting fusion of the stabilized vertebrae. It should be understood that by restricting 'relative' motion of vertebrae 12 and 14, vertebrae 12 and 14 can not rotate or translate independently, however, the vertebrae are capable of simultaneous rotation and translation.

Engagement between projection 24 of superior plate 20 and its complimentary recess 33 of inferior plate 30 limits flexion, extension, torsion, lateral motion, and shear motion of the respective vertebrae. First, because little or no radial gap exists between projection 24 and its complimentary recess 33, the vertebrae are limited from flexion, extension, lateral motion, and shear motion with respect to each other. Preferably, the tolerances of projection 24 and its complimentary recess 33 are such that projections 24 can freely telescope along axis 100 without translating, twisting, wobbling or pivoting in other directions. Second, because device 10 includes more than one projection 24 positioned in a recess, superior plate can not rotate with respect to inferior plate 20, thus limiting relative torsion of vertebrae 12 and 14. Thus, by virtue of the device's aforementioned dimensional and structural constraints, superior plate 20 can not rotate or translate with respect to inferior plate 20 in any direction other than along axis 100 to a significant extent.

Figure 1C:
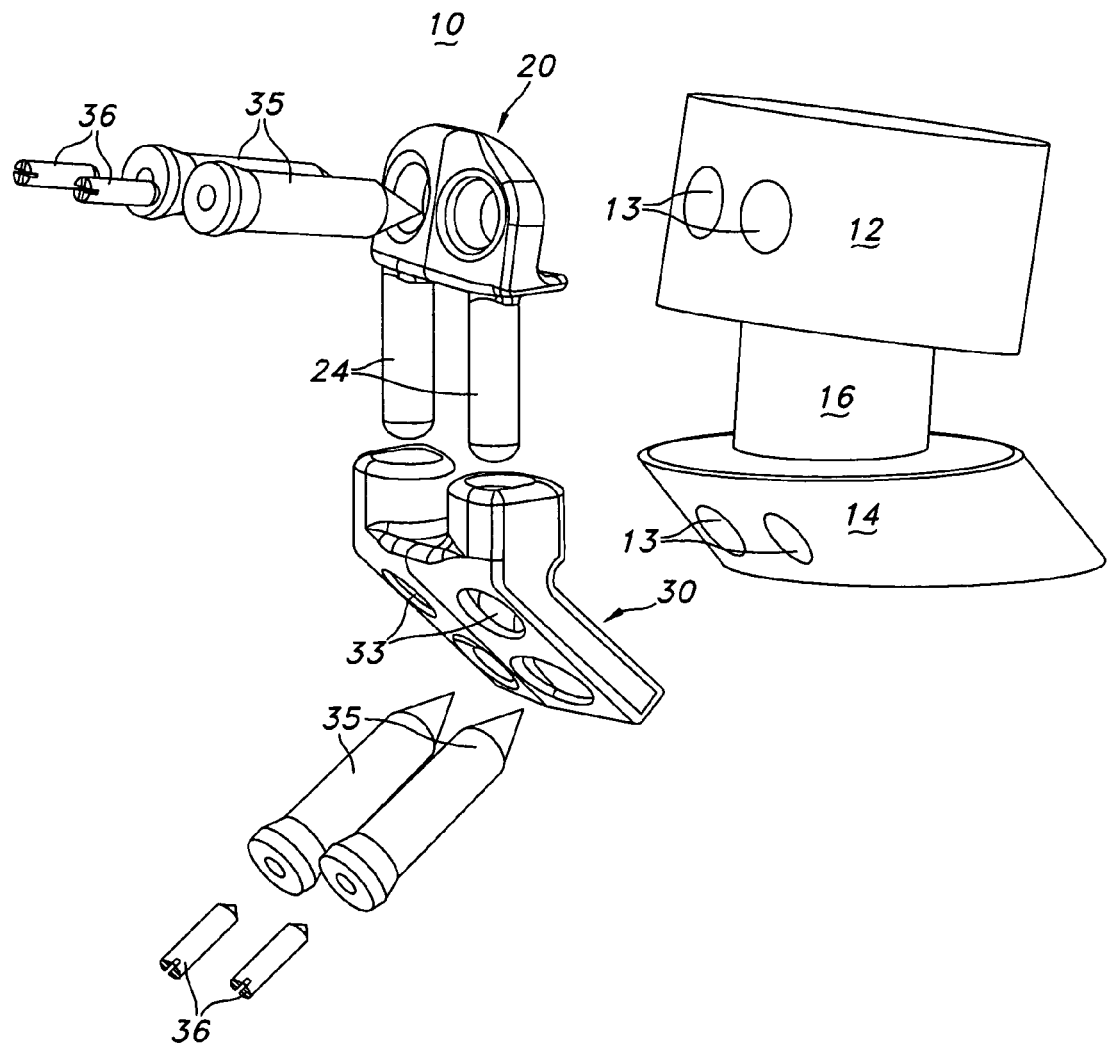
FIG. 1C is a perspective view of the dynamic vertebral stabilization device and the L5 and S1 vertebrae shown in FIG. 1A, wherein the stabilization device is shown exploded.

Referring now to FIG. 1C, in one embodiment of the use of this invention, prior to installing device 10, the degenerated disc between vertebrae 12 and 14 is removed and replaced with ALIF spacer 16 (or other spacer). A series of pilot holes 13 are drilled in the vertebrae to accommodate fasteners 35 utilized to mount device 10 to the spine. The pilot holes 13 may be tapped (i.e., threaded), or, alternatively, fasteners 35 may be self-tapping (i.e., self-threading). However, depending upon the fastener style, the fasteners may be drilled into the vertebrae in the absence of threaded or unthreaded pilot holes.

Once the spacer 16 is inserted between the adjacent vertebrae and pilot holes 13 are drilled and tapped (optional step), projections 24 of superior plate 20 are positioned through complimentary recesses 33 of inferior plate 30 in preparation for mounting device 10 to the vertebrae. The countersunk holes 25 of superior plate 30 are then aligned with pilot holes 13 of vertebrae 12 (if available), and countersunk holes 38 of inferior plate 30 are aligned with pilot holes 13 of vertebrae 12 (if available). Each fastener 35 is threaded into a pilot hole until the chamfered head seats on the countersunk surface of the hole (items 25 and 38). The connection between fasteners 35 and the plates in the embodiment shown is polyaxial.

Figure 5:
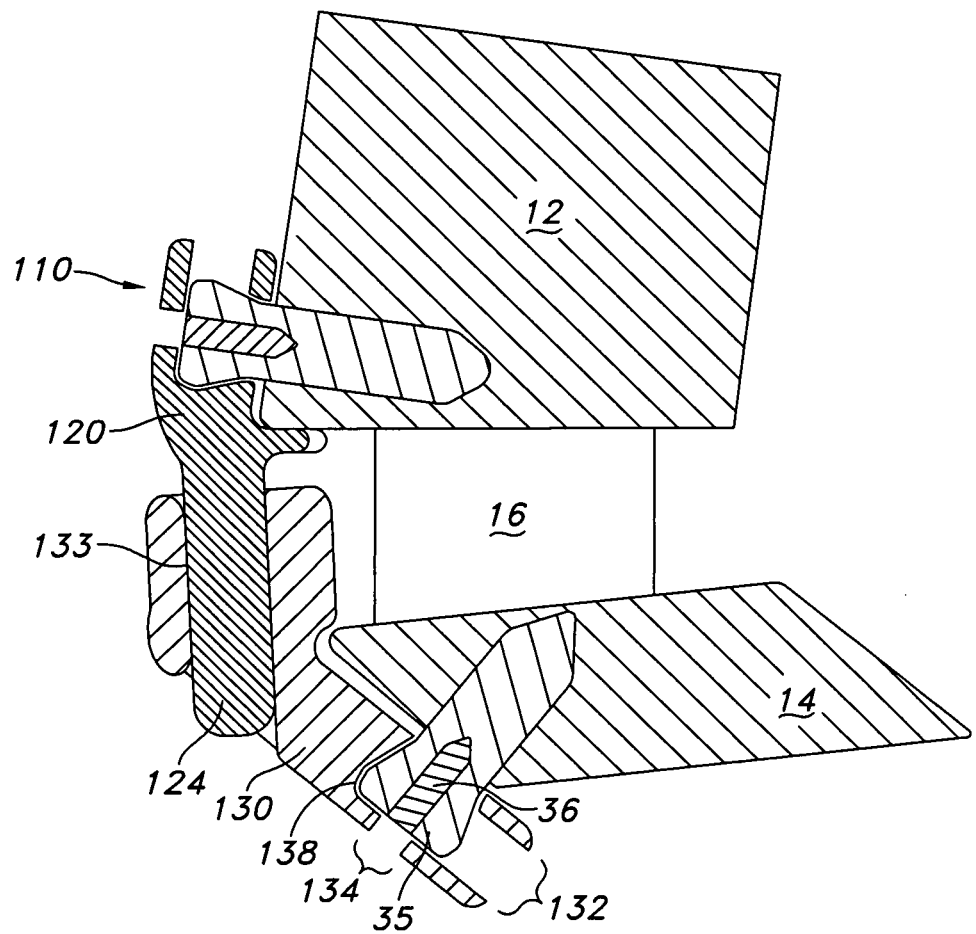
FIG. 5 is a cross-sectional view, similar to FIG. 1B, of another exemplary embodiment of a dynamic vertebral stabilization device.

Returning now to the embodiment discussed above, following installation of fasteners 35, a set screw 36 is threaded into the angled head of each fastener 35 in order to limit or prevent back-out, i.e. loosening, of fastener 35 in its respective hole. The set screw 36 is sized to elastically expand the angled head portion of fastener 35. Expanding the angled head portion of fastener 35 biases the angled head portion of fastener 35 in a state of tension with the countersunk surfaces of holes 25 and 38. Because the angled head portion of fastener 35 is biased in a state of tension, the male threads of fastener 35 are maintained in a state of compression against the female threads (not explicitly shown) of the vertebrae, thereby increasing the coefficient of friction between the mated threads. Thus, by increasing the coefficient of friction between the mated threads, fastener 35 is less likely to back-out of the threaded hole of the vertebrae. In addition to the above, the stabilization device shown in FIG. 5 is configured to further limit back-out of fastener 35.

Figure 2:
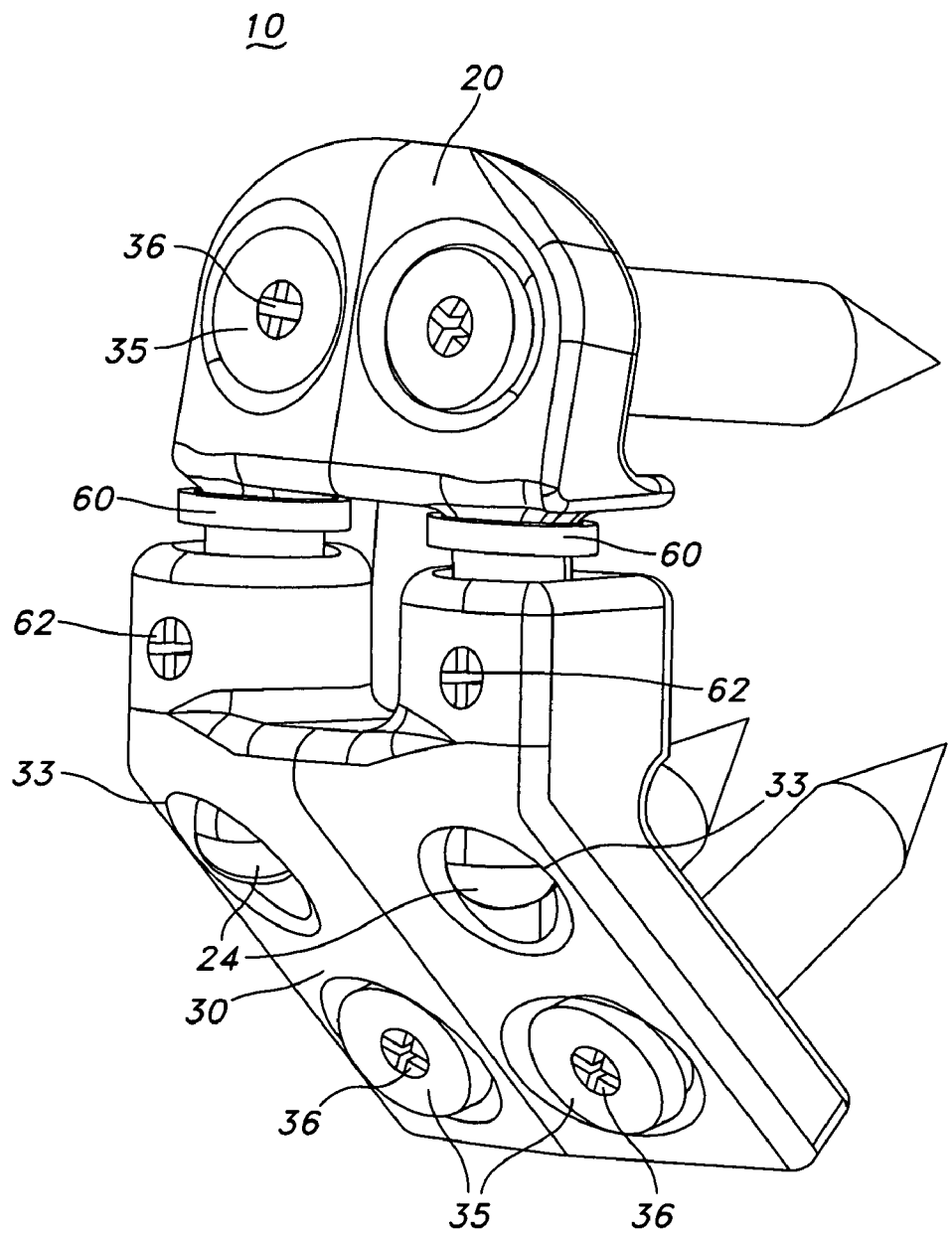
FIG. 2 is a front perspective view of the dynamic vertebral stabilization device shown in FIG. 1A, including optional components not shown in FIG. 1A.

Referring now to FIG. 2, a perspective view of an assembled stabilization device 10 is shown. The spine is omitted for the purpose of clarity. The ends of projection 24 are shown extended through recess 33 of inferior plate 30. The recess 33 is optionally a thru-hole, i.e., recess 33 extends through the entire body of inferior plate 20 along axis 100. Consequently, travel of projection 24 along axis 100 is not limited by any surface of recess 33.

The recess 33 of inferior plate 30 was incorporated into the design to address the need for a modular vertebral stabilization device that has sufficient versatility to accommodate varying patient anatomy. A projection 24 of any reasonable length may be engaged with recess 33 of inferior plate 30 without concern of projection 24 "bottoming-out" on a surface of inferior plate 30. Therefore, a minimum assortment of inferior plates and superior plates are required to accommodate a large cross-section of ALIF spacers and patient anatomy.

A modular stabilization device is particularly beneficial from the manufacturing perspective, because fewer different superior and inferior plate sizes represents lower tooling costs. Furthermore, limiting the stabilization device 10 to a smaller number of parts that must be handled and stocked would conceivably decrease costs associated with inventory control and inventory management.

In the exemplary embodiment of device 10 shown in FIG. 2, two damping elements 60, in the form of a hollow cylindrical collar, are positioned over projections 24 between plates 20 and 30. The damping elements 60 are only shown in FIG. 2, because the damping elements are optional components of device 10. Damping element 60 is positioned to limit compression of device 10 along axis 100. Specifically, damping element 60 limits the travel of superior plate 30 relative to inferior plate 20 in the direction of compression along axis 100. Although not shown, the thickness of damping element 60 may be sized to prevent travel of inferior plate 30 relative to superior plate 20 along axis 100 altogether.

The exemplary device 10 may also optionally include one or more fasteners 62 (two shown in FIG. 2) to prevent or restrict the travel of the inferior plate 30 relative to superior plate 20 along axis 100. The fastener 62 is inserted between the plates, i.e., fastener 62 is threaded within a recess disposed in inferior plate 30, and one end of fastener 62 is inserted within a hole or elongated slot (not shown) disposed in projections 24 of superior plate 20. Engagement between fastener 62 and the boundary of the hole or elongated slot (not shown) prevents or limits the relative travel of the plates along axis 100. The fastener 62 may be a grub screw, for example, or any other fastening means. The fasteners 62 are optional components of device 10, and are solely illustrated in FIG. 2.

In this exemplary embodiment, damping element 60 embodies a ring, however in another embodiment damping element may be a spring, bushing, block or other component. The element 60 is optionally formed from polyetheretherketone (referred to as PEEK) material. PEEK is a particularly desirable material by virtue of its x-ray translucency. It should be understood that damping element 60 is an optional component of device 10, as other embodiments of the device do not include a damping element.

Figure 3A:
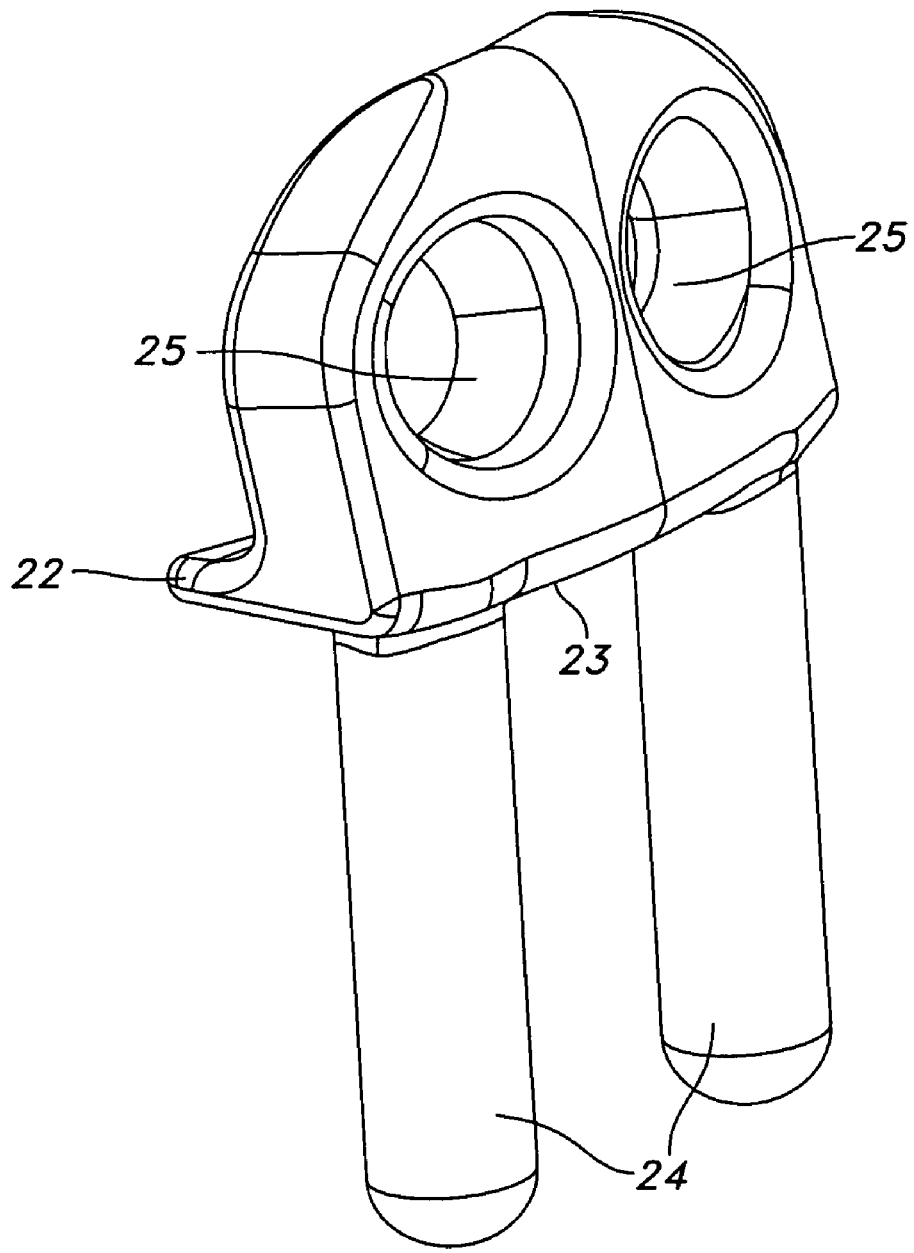
FIG. 3A is a front perspective view of the superior plate of the dynamic vertebral stabilization device shown in FIG. 2.
Figure 3B:
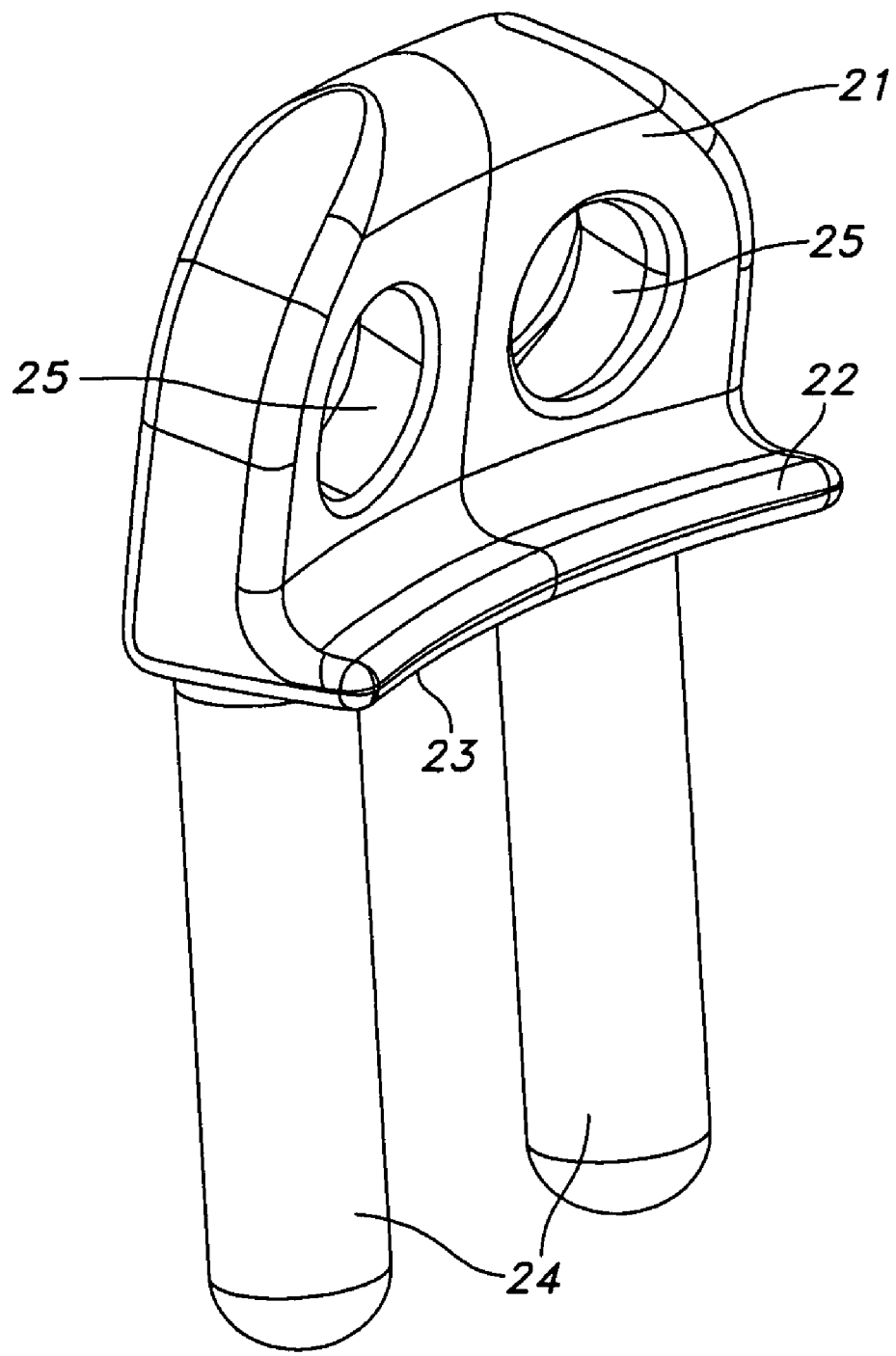
FIG. 3B is a rear perspective view of the superior plate of the dynamic vertebral stabilization device shown in FIG. 3A.

Referring now to FIGS. 3A and 3B, two perspective views of superior plate 20 are shown according to this exemplary embodiment. The top edge of superior plate 20 (opposite projections 24) includes generously rounded corners to limit or wholly prevent contact with the bifurcating greater vessel (aorta) that lies just superior to the vertebral body in the region of L4 and L5.

The vertebral mating surface 21 of plate 20 is contoured to complement the curvature of the anterior surface of vertebrae 12. In general, the plates embody curvature in two planes, i.e., sagittal and coronal, to complement the contours of vertebrae 12.

In the embodiment shown, a flange 22 extending from the bottom end of vertebral mating surface 21 on the posterior side of device 10 is positioned to bear on a lower edge of vertebrae 12, as shown in FIG. 1B. Similar to mating surface 21, flange 22 also conforms to the contours of vertebrae 12. The flange 22 absorbs a portion of the stress resulting from flexion, lateral motion, and shear motion, thereby diminishing the stress applied to fasteners 35.

Two projections 24 extend below planar surface 23 of superior plate 20. The gap between projections 24 (defining the width of graft window 50) may be of any dimension suitable for a surgeon to view spacer 16 or insert a tool to readjust the position of ALIF spacer 16 between vertebrae 12 and 14.

The exemplary projections 24 are cylindrically shaped to engage the cylindrically shaped recesses 33 of the inferior plate. The diameter of projections 24 is preferably adequate to limit fracture of projection 24 under applied stress caused by flexion, extension, torsion, lateral motion, and shear motion of the respective vertebrae. Because recesses 33 are thru-holes, projections 24 may be of any reasonable length.

Although the illustrated projections 24 are cylindrically shaped, the projections may embody any shape, such as square or hexagonal, so long as the arrangement of projection 24 and recess 33 permits compression and expansion of spacer 16, while limiting flexion, extension, lateral motion, and shear motion of the stabilized vertebrae. Preferably, the cross-sectional shape of recess 33 compliments the cross-sectional shape of the projections (i.e., cylindrical/cylindrical, square/square, etc.). As mentioned above, plate 20 includes at least two projections 24 to limit torsion of vertebrae 12 and 14, with respect to each other. However, if the projection 24 is square, hexagonal, or other shape of non-circular cross-section, only one projection 24 is required to limit torsion of the stabilized vertebrae.

The two countersunk holes 25 of plate 20 bestow two significant advantages over non-countersunk holes. First, the countersunk holes limit or prevent the angled head of fasteners 35 from protruding beyond the exterior surface of device 10 so as to avoid contact with blood vessels or muscles. Second, the countersunk holes cooperate with set screw 36 to limit or prevent back-out of the fasteners, as explained previously with reference to FIG. 1B. The aforementioned advantages of countersunk holes 25 also apply to countersunk holes 38 of inferior plate 30.

Figure 4A:
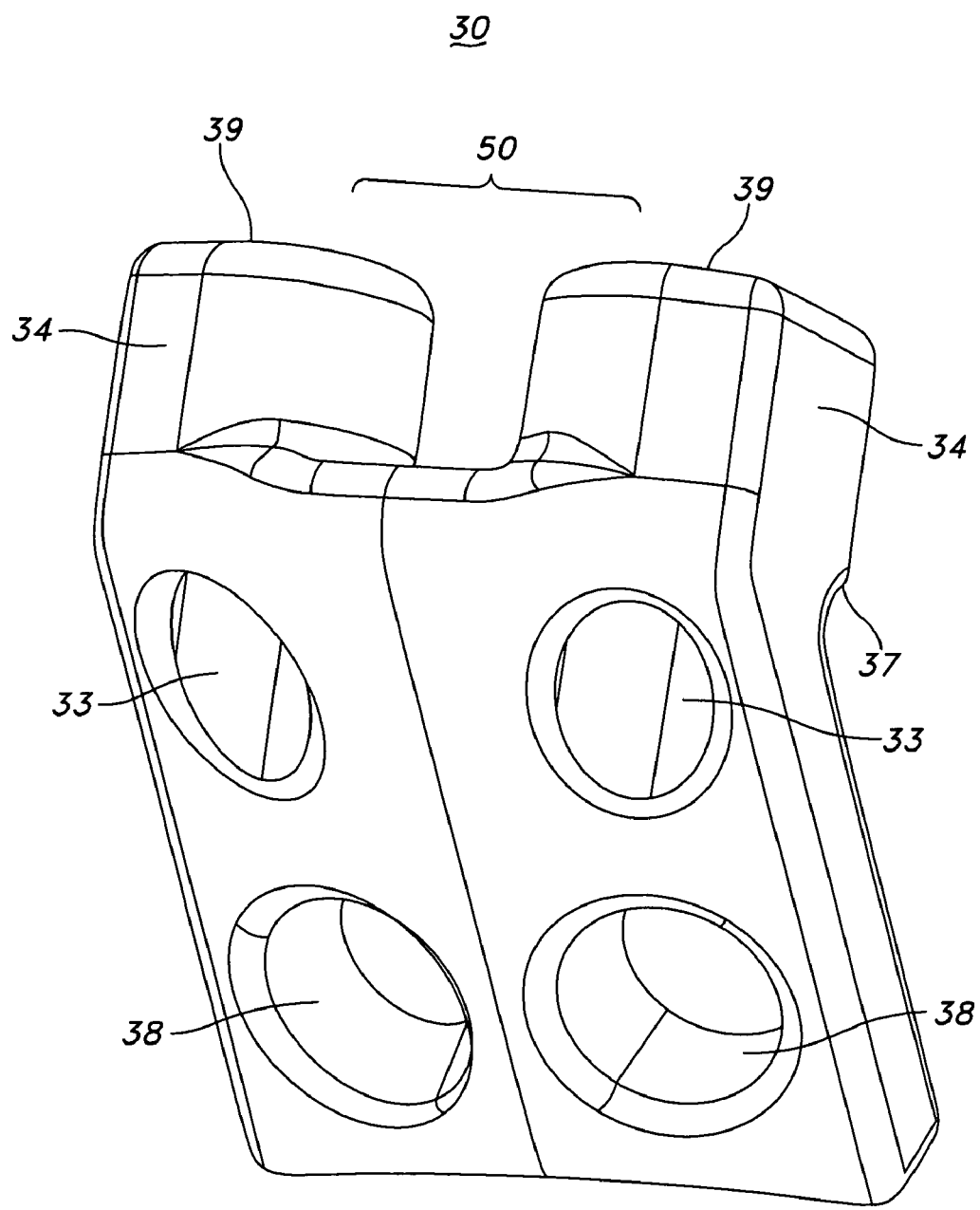
FIG. 4A is a front perspective view of the inferior plate of the dynamic vertebral stabilization device shown in FIG. 2.
Figure 4B:
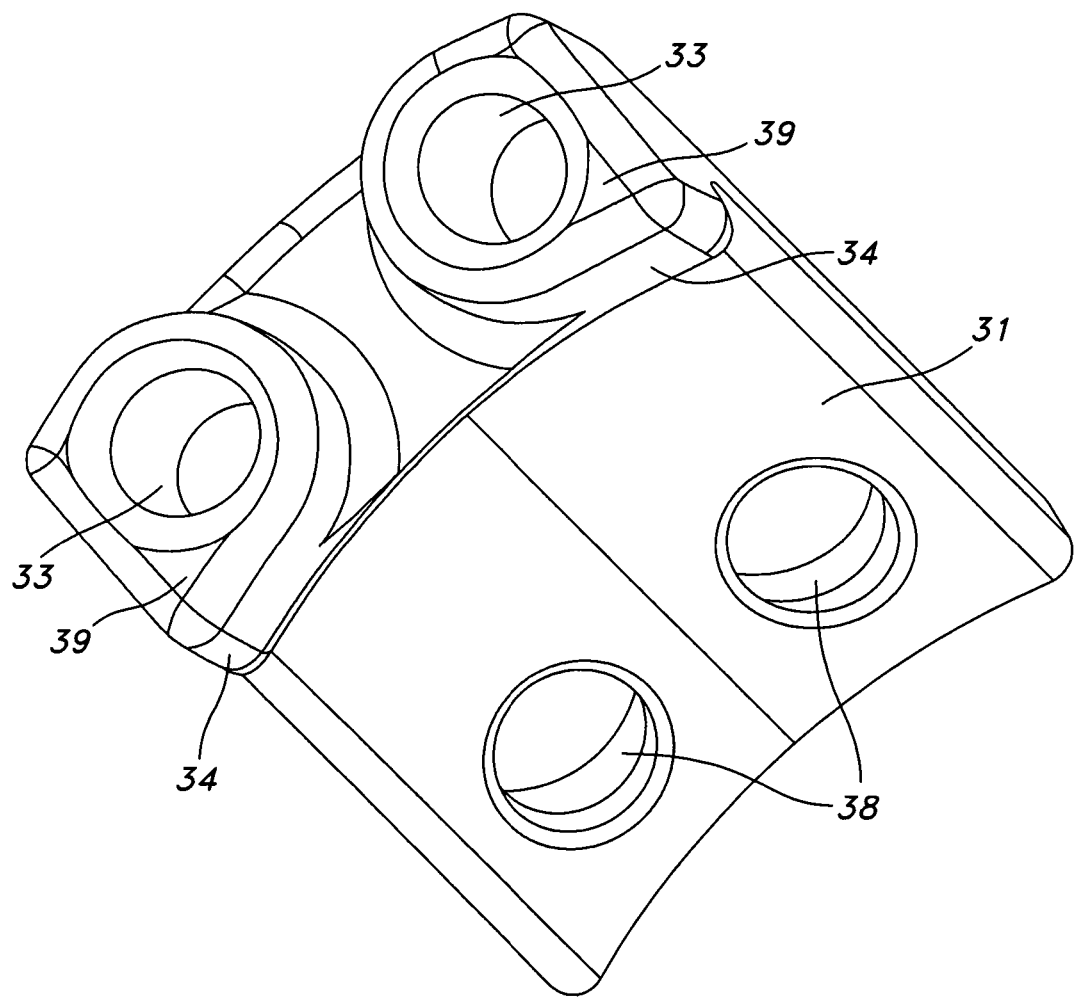
FIG. 4B is a rear perspective view of the inferior plate of the dynamic vertebral stabilization device shown in FIG. 4A.

Referring now to FIGS. 4A and 4B, two perspective views of inferior plate 30 are shown. Each recess 33 of inferior plate 30 extends from planar surface 39 to rear surface 31, passing through boss 34. The recess 33 may embody a non-circular or circular shape (as shown). However, it should be understood that the shape of recess 33 must accommodate the body of projection 24, such that device 10 permits compression and expansion of spacer 16, and limits flexion, extension, lateral motion, and shear motion of the stabilized vertebrae.

The recesses 33 are carried in two bosses 34 provided at the top of inferior plate 30. The inner walls of the two opposing bosses 34 define the width of window 50, and are sized to carry projections 24 of superior plate 20. Because bosses 34 carry projections 24, they are exposed to resultant stress from flexion, extension, torsion, lateral motion, and shear motion of the respective vertebrae. The bosses 34 are sized such that they are large enough to resist fracture, yet are sufficiently slender to provide an adequately sized window 50 therebetween.

A flange 37 is disposed at the base of bosses 34 on the posterior side of device 10, and is positioned to bear on a top edge of vertebrae 14, as shown in FIG. 1B. Similar to flange 22, flange 37 absorbs a portion of the stress resulting from flexion, lateral motion, and shear motion, thereby diminishing the stress applied to fasteners 35.

The contoured shapes of vertebral mating surface 31 and flange 37 of plate 30 are tailored to complement the contoured surfaces of vertebrae 14. The slope of vertebral mating surface 31, as shown in the non-limiting, exemplary figures, is particularly suited for mounting to the S1 vertebrae. However, the slope of vertebral mating surface 31 may be altered to enable inferior plate 30 to be mounted to any other vertebrae.

Referring now to FIG. 5, another exemplary embodiment of a vertebral stabilization device 110 is shown. The device 110 illustrated in FIG. 5 is similar to device 10 of FIG. 1B, however, inferior plate 130 and superior plate 120 are configured to limit back-out of fasteners 35.

In this exemplary embodiment, superior plate 120 and inferior plate 130 are designed to prevent fasteners 35 from backing out of their respective holes 138. Inferior plate 130 is similar to inferior plate 30, with the exception of slot 132 and aperture 134. In assembly, the head of fastener 35 is captivated within slot 132 and seated on countersunk surface 138, as shown, thereby limiting or preventing back-out of the fastener 35. The aperture 134 is provided in inferior plate 130 for access to the set screw 36, so that the fastener 35 may be tightened, adjusted or removed. Accordingly, aperture 34 is preferably large enough to accommodate a hand tool, such as the end of a screwdriver, yet is small enough to constrain at least a portion of the head of fastener 35. In assembly, the head of fastener 35 slides through slot 132, and the fastener 35 is threaded into vertebrae 14.

The superior plate 120 includes a slot similar to slot 132 of inferior plate 130 to achieve the same purpose. Numerous variations of slot 132, aperture 134, and hole 138 are envisioned to limit or prevent back-out of fastener 35. Moreover, fastener 35 may be a locking-type fastener, or the fastener may be rigidly mounted to the plate to prevent back-out.

The vertebral stabilization devices described thus far are adapted for constraining motion of two adjacent vertebrae 12 and 14. However, in another exemplary embodiment, a vertebral stabilization device may be adapted for constraining motion of three or more adjacent vertebrae, as described with reference to FIG. 6.

Figure 6:
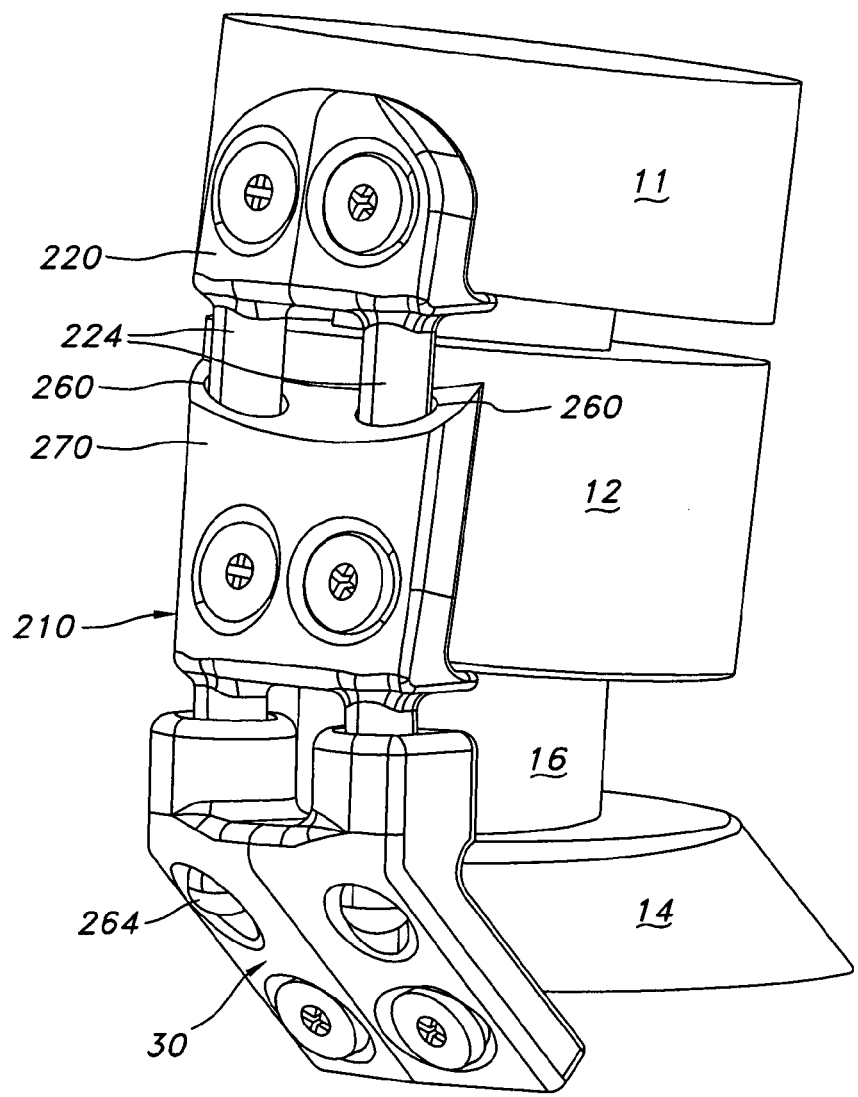
FIG. 6 is a perspective view of another exemplary embodiment of a dynamic vertebral stabilization device mounted to the L5 and S1 vertebrae according to aspects of this invention.

Referring now to FIG. 6, another exemplary embodiment of a vertebral stabilization device 210 is shown. In this exemplary embodiment, vertebral stabilization device 210 comprises inferior plate 30, intermediate plate 270, and superior plate 220. The vertebral stabilization device 210 is adapted for constraining motion of three adjacent vertebrae, i.e., S1 vertebrae (item 14), L5 vertebrae (item 12), and L4 vertebrae (item 11). The inferior plate 30 is mounted to S1 vertebrae 14, intermediate plate 270 is mounted to L5 vertebrae 12, and superior plate 220 is mounted to L4 vertebrae 11, as shown.

Similar to the previously described vertebral stabilization devices, vertebral stabilization device 210 permits compression and expansion of vertebrae 11, 12 and 14, while limiting flexion, extension, torsion, lateral motion, and shear motion of adjacent vertebrae 11, 12 and 14, relative to each other.

The superior plate 220 is similar to superior plate 20, however, superior plate 220 is mounted to vertebrae 11, thus, the size and shape of superior plate 220 may vary from the size and shape of superior plate 20 to conform to the contours of L4 vertebrae 11.

The intermediate plate 220 is similar to superior plate 20 shown in FIG. 1A, however, intermediate plate 270 includes an extended body portion, and two recesses 260 disposed within the extended body portion. Similar to the engagement of projection 24 and recess 33 of device 10, projections 224 of superior plate 220 slide within recesses 260 of intermediate plate 270. Engagement between projections 224 and recesses 260 permits compression and expansion of vertebrae 11 and 12, while limiting flexion, extension, torsion, lateral motion, and shear motion of adjacent vertebrae 11 and 12, relative to each other. Although three plates are shown in this embodiment, the vertebral stabilization device may include any number of plates. Alternative embodiments of device 210 are also envisioned. For example, recesses 260 may be disposed in superior plate 220 and intermediate plate 270 may include projections 224 to achieve the same purpose.

The plates may be formed from Titanium, Titanium alloy Ti-6AI-4V, Stainless Steel, PEEK polymer, poly-L-lactic acid polymer (commonly referred to as PLLA), or any other appropriate bio-compatible material. Titanium alloy Ti-6AI-4V is generally the most bio-compatible of all metals, and possesses high strength, low density, flexibility, low modulus of elasticity, and a low thermal coefficient of expansion. Other advantages of Ti-6AI-4V are its decreased interference with metal detectors and magnetic resonance imaging (MRI) used for projection operative evaluation. PEEK material is particularly well suited for spinal fusion applications because of its x-ray translucency properties. Alternatively, the device components may be formed from a resorbable material such as copolymer 70/30 PLLA. The surfaces of the plates are desirably smooth to limit friction caused by rubbing contact between a plate and a blood vessel. Although not explicitly shown, a thin membrane or plastic film may be applied to the surfaces of the plates to reduce the friction between the plates and a vessel.

While exemplary embodiments of the invention have been shown and described herein, it will be understood that such embodiments are provided by way of example only. Numerous variations, changes and substitutions will occur to those skilled in the art without departing from the spirit of the invention. Examples of such variations are described below.

Although device 10, as shown, is particularly suited to mount to the L5 and S1 vertebrae, device 10 may be mounted to any adjacent cervical, thoracic, lumbar or sacral vertebrae of the spine, with minor modifications.

Furthermore, in another exemplary embodiment, not illustrated herein, the superior plate of the device includes only one projection, and the inferior plate includes only one complimentary recess. In such an embodiment, the projection and recess would have non-circular, keyed shapes in order to restrict the keyed projection from rotating in the keyed hole.

In yet another exemplary embodiment, not illustrated herein, the projections are provided on the inferior plate and the recesses are provided on the superior plate to achieve the same purpose. Accordingly, the plates are referred to as 'first' and 'second' plates in the appended claims, as opposed to 'superior' and 'inferior' plates, In still another exemplary embodiment, not illustrated herein, each plate is mounted to a vertebrae by a single fastener and set screw. Alternative arrangements of fastener and/or set screws are contemplated.

Accordingly, it is intended that the appended claims cover all such variations as fall within the spirit and scope of the invention.

What is claimed:

1. A dynamic vertebral stabilization device for constraining motion of adjacent vertebrae, the stabilization device comprising:
 a first plate for positioning against a first vertebra, the first plate having a vertebral mating surface conforming to a first plane, and at least one elongated projection extending away from the vertebral mating surface, the at least one elongated projection having a free end; and
 a second plate for positioning against a second vertebra, the second plate having a vertebral mating surface conforming to a second plane that extends at an obtuse angle with respect to the first plane, and at least one thru-hole that enters the second plate through a first side of the second plate and exits the second plate through a second side of the second plate, the at least one thru-hole having a longitudinal axis forming an obtuse angle with the second plane, the at least one projection slideably carried in the at least one thru-hole to a position in which the at least one projection is inserted in the at least one thru-hole with the free end extending out of the at least one thru-hole and projecting from the second side of the plate, the at least one thru-hole allowing passage of the at least one projection through the second plate without bottoming out in the second plate, wherein a longitudinal axis of said first plate is non-parallel with respect to a longitudinal axis of said second plate, and wherein said first plate includes a flange extending from its respective vertebral mating surface for positioning on a substantially planar surface or edge of a sacral vertebra, and wherein, in an assembled and installed state of the dynamic vertebral stabilization device, the dynamic vertebral stabilization device is configured to facilitate both compressive and expansive relative motion of the adjacent vertebrae without restriction.

2. The dynamic vertebral stabilization device of claim 1 wherein a longitudinal axis of said first plate is non-parallel with respect to a longitudinal axis of said second plate, and wherein an angle separates said longitudinal axis of said first plate from said longitudinal axis of said second plate, the angle being between about 110 degrees and about 170 degrees, wherein, in an assembled and installed state of the dynamic vertebral stabilization device, the dynamic vertebral stabilization device is configured to facilitate both compressive and expansive relative motion of the adjacent vertebrae without restriction.

3. The dynamic vertebral stabilization device of claim 2, wherein the second plate comprises at least two thru-holes, and said first plate includes at least two projections, wherein each projection e is configured to travel in a corresponding thru-hole in said second plate.

4. The dynamic vertebral stabilization device of claim 3 wherein a window is defined between said projections for viewing a spinal disc between the adjacent vertebrae.

5. The dynamic vertebral stabilization device of claim 2 wherein an angle separating said longitudinal axis of said first plate from said longitudinal axis of said second plate is from about 130 degrees to about 150 degrees.

6. The dynamic vertebral stabilization device of claim 1 wherein said second plate is configured to be fixedly coupled to a lumbar vertebra.

7. The dynamic vertebral stabilization device of claim 1 wherein said second plate includes a flange extending from its respective vertebral mating surface for positioning on a substantially planar surface or edge of the lumbar vertebra.

8. The dynamic vertebral stabilization device of claim 1 wherein the at least one projection is configured to travel in the at least one thru-hole along a single axis.

9. The dynamic vertebral stabilization device of claim 1 further comprising a damping element positioned between said first plate and said second plate to limit compressive or expansive motion of said stabilization device.

10. The dynamic vertebral stabilization device of claim 9 wherein said damping element is a collar positioned about the at least one projection and sandwiched between said first plate and said second plate.

11. The dynamic vertebral stabilization device of claim 1 further comprising a travel limiting device disposed between said first plate and said second plate to limit compressive or expansive motion of said stabilization device.

12. The dynamic vertebral stabilization device of claim 11 wherein said travel limiting device is a grub screw positioned within or through said second plate and said at least one projection of said first plate.

13. The dynamic vertebral stabilization device of claim 1 wherein said device limits torsional, lateral, shear and flexural motion of the adjacent vertebrae with respect to each other.

14. The dynamic vertebral stabilization device of claim 1 further comprising a third plate slideably coupled with either said first plate or said second plate.

15. The dynamic vertebral stabilization device of claim 14, said third plate including a projection configured to travel in a thru-hole of said second plate or a thru-hole of said first plate.

16. A dynamic vertebral stabilization device for constraining motion of adjacent vertebrae, the stabilization device comprising:

a first plate for positioning against a first vertebra, the first plate having a vertebral mating surface conforming to a first plane, and at least one elongated projection extending away from the vertebral mating surface, the at least one elongated projection having a free end; and a second plate for positioning against a second vertebra, the second plate having a vertebral mating surface conforming to a second plane that extends at an obtuse angle with respect to the first plane, and at least one thru-hole that enters the second plate through a first side of the second plate and exits the second plate through a second side of the second plate, the at least one thru-hole having a longitudinal axis forming an obtuse angle with the second plane, the at least one projection displaceable into the at least one thru-hole, the at least one thru-hole allowing passage of the at least one projection through the second plate without bottoming out in the second plate, wherein a longitudinal axis of said first plate is non-parallel with respect to a longitudinal axis of said second plate, and wherein said first plate includes a flange extending from its respective vertebral mating surface for positioning on a substantially planar surface or edge of a sacral vertebra, and wherein, in an assembled and installed state of the dynamic vertebral stabilization device, the dynamic vertebral stabilization device is configured to facilitate both compressive and expansive relative motion of the adjacent vertebrae without restriction.

* * * * *